(12) United States Patent
Bau et al.

(10) Patent No.: US 7,824,620 B2
(45) Date of Patent: Nov. 2, 2010

(54) NANO- AND MICRO-SCALE STRUCTURES: METHODS, DEVICES AND APPLICATIONS THEREOF

(75) Inventors: Haim H. Bau, Swarthmore, PA (US); Byong M. Kim, East Brunswick, NJ (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 1363 days.

(21) Appl. No.: 11/231,425

(22) Filed: Sep. 21, 2005

(65) Prior Publication Data

US 2006/0115971 A1 Jun. 1, 2006

Related U.S. Application Data

(60) Provisional application No. 60/611,624, filed on Sep. 21, 2004.

(51) Int. Cl.
*B01L 3/02* (2006.01)

(52) U.S. Cl. .................... 422/100; 422/98; 422/99; 252/502; 438/591; 73/866.5

(58) Field of Classification Search ........... 422/98–100; 252/502; 438/591; 73/866.5
See application file for complete search history.

(56) References Cited

U.S. PATENT DOCUMENTS 5,788,166 A 8/1998 Valaskovic et al. .......... 239/708

OTHER PUBLICATIONS

Bau, H.H., et al., "Fabrication of nanofluidic devices and the study of fluid transport through them," *Nanofabrication: Technologies, Devices, & Applications*, 2004, 5592, W.Y.-C. Lai, et al. (Eds.), Phila. SPIE, 201-213.

Berg, M., et al., "Development and characterization of temperature-controlled microreactors for protein crystallization," *Acta Cryst.*, 2002, D58, 1643-1648.

Bradley, J.-C., et al., "Nanotubes synthesis using alumina template (a4)," *CPS: chemistry*/0303002, 2003, 1-6.

Moraes, M.F.D., et al. "Glass pipette-carbon fiber microelectrodes for evoked potential recordings,", *Brazilian J. Med. & Biol. Res.*, 1997, 30(11), 1319-1324.

Che, G., et al., "Chemical vapor deposition based synthesis of carbon nanotubes and nanofibers using a template method," *Chem. Mater.*, 1998, 10, 260-267.

DeRose, J.A., et al., "A comparative study of colloidal particles as imaging standards for microscopy," *J. of Microscopy*, 1999, 195 (Pt. 1), 64-78.

Doherty, L., et al., "Application of MEMS technologies to nanodevices," *Int. Symposium on Circuits & Systems*. Thailand, 2003, 4 pages.

(Continued)

*Primary Examiner*—Yelena G Gakh
*Assistant Examiner*—David Weisz
(74) *Attorney, Agent, or Firm*—Woodcock Washburn, LLP

(57) ABSTRACT

Disclosed are methods for fabricating integrated nano-scale and micro-scale structures. Also disclosed are carbon nanopipettes, shovels, and sheets made by these methods. Nano-scale and micro-scale structures fabricated by the disclosed methods are useful in a variety of application, for example, nanoelectrodes, functionalized probes for chemical and biological sensing, nanopipettes for fluid and macromolecule transfer, and devices for the dispensing and deposition of nanodrops.

17 Claims, 9 Drawing Sheets

OTHER PUBLICATIONS

Duff, D.G., et al., "A new hydrosol of gold clusters. 1. Formation and particle size variation," *Langmuir*, 1993, 9, 2301-2309.

Duval, J.F.L., et al., "Faradaic depolarization in the electrokinetics of the metal-electrolyte solution interface," *J. of Colloid & Interface Sci.*, 2003, 260, 95-106.

Evoy, S., et al., "Dielectrophoretic assembly and integration of nanowire devices with functional CMOS operating circuitry," *Microelectronic Eng.*, 2004, 75, 31-42.

Frens, G., Controlled nucleation for the regulation of the particle size in monodisperse gold suspensions, *Nature Physical Science*, 1973, 241, 20-22.

Gogotsi, Y., et al., "In situ multiphase fluid experiments in hydrothermal carbon nanotubes," *Appl. Phys. Lett.*, 2001, 79(1), 1021-1023.

Gogotsi, Y., et al., "Carbon nanopipes for nanofluidic devices and In-situ fluid studies," *NSF Nanoscale Sci. & Eng. Grantees Conf.*, 2003, 3 pages.

Ito, T., et al., "Simultaneous determination of the size and surface charge in individual nanoparticles using a carbon nanotube-based coulter counter," *Anal. Chem.*, 2003, 75, 2399-2406.

Kim, B.M., et al., "Optical microscope study of liquid transport in carbon nanotubes," *Nano Letts.*, 2004, 4(11), 2203-2208.

Kim, B.M., et al., "Filling carbon nanotubes with particles," *Nano Letts.*, 2005, 5(5), 873-878.

Kim, B.M., et al., "The fabrication of integrated carbon pipes with sub-micron diameters," *Nanotechnology*, 2005, 16, 1317-1320.

Kim, B.M., et al., "Nanotube fluidics & electronics," *Research page*, http://www.seas.upenn.edu/~byong/, 4 pages, 2005.

Kim, B.M., et al., "Hybrid fabrication of carbon nanotube—based devices and the measurement of ionic current through them," bau@seas.upenn.edu, *Paper ID No.* 0394, 2 pages.

Kluijtmans, S.G.J.M., et al., "Dynamics of uncharged colloidal silica spheres confined in bicontinuous porous glass media," *Langmuir*, 1997, 13, 4982-4987.

Knitter, R., et al., "Ceramic microreactors for heterogeneously catalysed gas-phase reactions," *Lab Chip*, 2004, 4, 378-383.

Millar, J., "Extracellular single and multiple unit recording with carbon fibre microelectrodes," http://www.qmw.ac.uk/~ugha014/making CFE.html, 1996, 1-7.

Miller, S.A., et al., "Electroosmotic flow in template-prepared carbon nanotube membranes," *J. Am. Chem. Soc.*, 2001, 123, 12335-12342.

Parthasarathy, R.V., et al., "Template synthesis of graphitic nanotubes," *Adv. Mater.*, 1995, 7(11), 896-897.

Peterson, D.S., et al., "Enzymatic microreactor-on-a-chip: protein mapping using trypsin immobilized on porous polymer monoliths molded in channels of microfluidic devices," *Anal. Chem.*, 2002, 74, 4081-4088.

Reed Business Information, "NSF NSE grantees report research progress," *Micro Nano*, 2004, 9(22), p. 20.

Riegelman, M., et al., "Nanofabrication of carbon nanotube (CNT) based fluidic device," *Proceed. of NATO-ASI Nanoengineered Nanofibrous Materials*, Guceri, S., et al. (Eds.), The Netherlands, 2004, 407-414.

Riegelman, M.A., "Dielectrophoretic assembly and integration of nanofluidic devices," Master's Thesis, *University of Pennsylvania*, 2004, ii-iv, 1-87.

Rossi, M.P., et al., "Environmental scanning electron microscopy study of water in carbon nanopipes," *Nano Letts.*, 2004, 4(5), 989-993.

Saleh, O.A., et al., "Quantitative sensing of nanoscale colloids using a microchip coulter counter," *Rev. of Scientific Instruments*, 2001, 72(12), 4449-4451.

Spherotech, Inc., *III. Product and Price Information*; 1. SPHERO™ *Polystyrene Particles*, http://spherotech.com/PolParIn.pclf, downloaded Jul. 12, 2005, 4-7.

Stöber, W., et al., "Controlled growth of monodisperse silica spheres in the micron size range," *J. of Colloid & Interface Sci.*, 1968, 26, 62-69.

Sun, L., et al., "Single carbon nanotube membranes: a well-defined model for studying mass transport through nanoporous materials," *J. Am. Chem. Soc.*, 2000, 122, 12340-12345.

Sun, L., et al., "Fabrication and characterization of single pores for modeling mass transport across porous membranes," *Langmuir*, 1999, 15, 738-741.

Supple, S., et al., "Rapid imbibition of fluids in carbon nanotubes," *Phys. Rev. Lett.*, 2003, 90(21), 214501-1-214501-4.

Wagner, J., et al., "Generation of metal nanoparticles in a microchannel reactor," *Chem. Eng. J.*, 2004, 101, 251-260.

Watts, P., et al., "Microfluidic combinatorial chemistry," *Curr. Opinion in Chem. Biol.*, 2003, 7, 380-387.

Yamamoto, T. et al., "PDMS-glass hybrid microreactor array with embedded temperature control device. Application to cell-free protein synthesis," *Lab Chip*, 2002, 2, 197-202.

U.S. Appl. No. 11/1777,111, filed Jul. 8, 2005, Bau.

Figure 4
(a) Start with a glass capillary
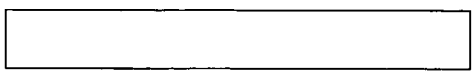
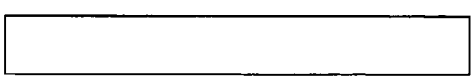
(b) Coat the glass with carbon
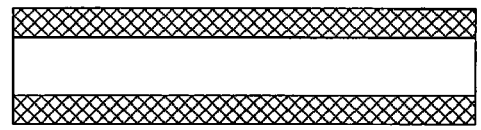
(c) Remove the carbon outside the glass
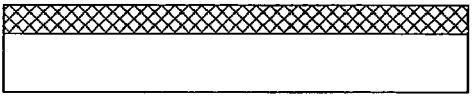
(d) Remove the glass locally to expose the carbon inside
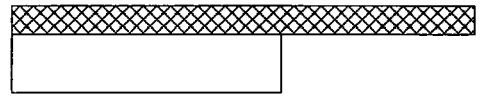

Scanning Electron Micrograph of CNT-Based Pipettes. Insets: a) Scanning and b) Transmission

Figure 8
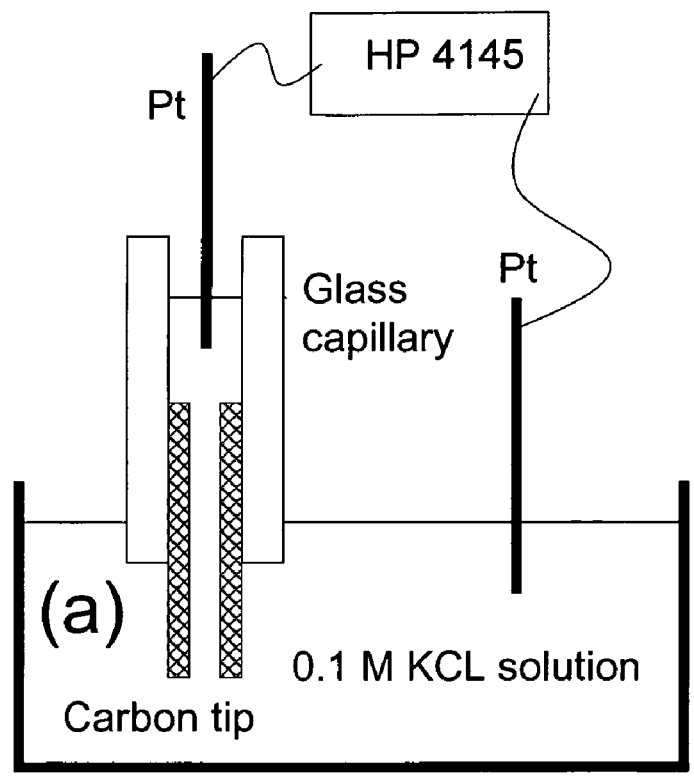
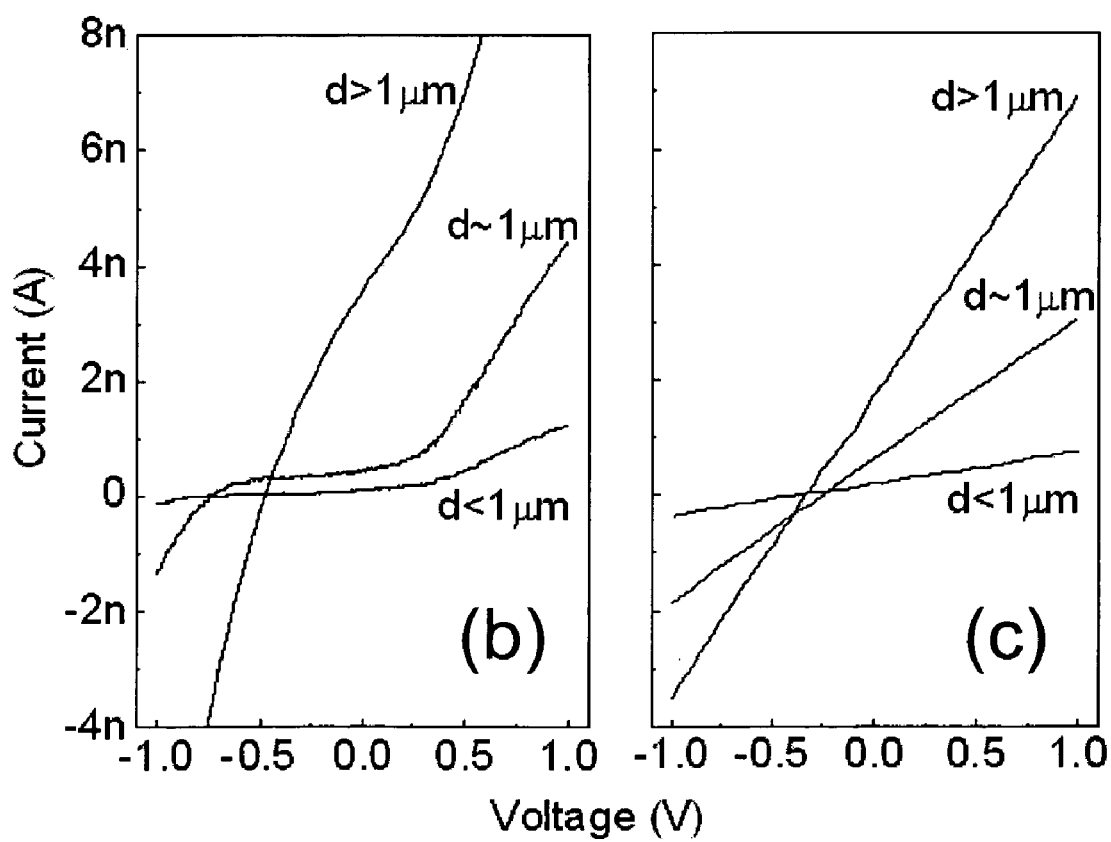

NANO- AND MICRO-SCALE STRUCTURES: METHODS, DEVICES AND APPLICATIONS THEREOF

CROSS REFERENCE TO RELATED APPLICATIONS

This application claims the benefit of U.S. Provisional Application Ser. No. 60/611,624, filed Sep. 21, 2004, the entirety of which is incorporated by reference herein.

STATEMENT OF GOVERNMENT INTEREST

The invention was made with U.S. Government support. The Government may have certain rights in the invention under NSF NIRT Program Grant No. CTS-0210579.

FIELD OF THE INVENTION

The field of the invention pertains to the fabrication of integrated structures in the nano- and micro-scale. The field of the invention also pertains to nano-scale and micro-scale integrated structures and their uses in nano-fluidic and micro-fluidic applications.

BACKGROUND

Transporting fluids at sub-micron length scales is becoming increasingly important in a wide range of applications. For example, study of the transport of liquids through carbon nanopipettes has increased due to interest in understanding the motion of highly confined fluids and the prospect of building nanofluidic devices from nanopipes in the future. The flow of liquids through carbon pipes of sub-micron diameter has been studied by Miller et al, 2001 *J. Am. Chem. Soc.* 123 12335, which describes electro-osmotic flow in carbon-pipe-based membranes formed in the pores of perforated alumina membranes. A Coulter counter has been produced by Sun et al, 2000 *J. Am. Chem. Soc.* 122 12340, and Ito et al, 2003 *Anal. Chem.* 75 2399, which describe embedding individual carbon pipes with diameters of a few hundred nanometers in an epoxy layer. Nanoassembly and microfabrication techniques have been applied to produce nanofluidic devices in Bau et al, 2004 *Nanofabrication: Technologies, Devices, and Applications* (*Proc. SPIE* vol 5592) ed. W Y-C Lai, S Pau and O D Lopez (Philadelphia, Pa.,: SPIE) 201-13 (Invited Paper). Gogotsi et al, 2001 *Appl. Phys. Lett.* 79 1021, has used a transmission electron microscope to study the behavior of thermally actuated liquids that are confined in hydrothermally synthesized carbon nanotubes. Rossi et al, 2004 *Nano Lett.* 4 989, describes the use of a scanning electron microscope to study the wetting properties of carbon tubes with diameters of 50 to 300 nanometers grown in alumina pores. Optical microscopes have been used to study capillary filling, condensation, and evaporation of liquids in Kim et al, 2004 *Nano Lett.* 4 2203, and the filling of particles into sub-micron, alumina-grown nanotubes has been studied with a fluorescence microscope in Kim et al, 2005 *Nano Lett.* 5 873.

The production of nano- and micro-sized structures typically requires a difficult, and often unattainable, assemblage of multiple components. Existing technology cannot readily probe biological cells and organelles or provide for fluid and macromolecule transfer in the nano-scale. A typical method of producing a carbon-fiber electrode, for example, requires the difficult task of inserting a carbon fiber into an electrode glass tube and affixing it to a single strand conductor using conducting silver paint. FIG. 1 is an example of this process. The end of the glass is typically sealed around the carbon fiber by using a heating coil as shown in FIG. 2. Producing devices through these type of manual processes is painstaking and not applicable to mass production. Methods to fabricate probes on the nano- and micro-scale have been desired in the art. Accordingly, there remains the need to provide a variety of devices at the nano- and micro-scales using processes that are efficient and commercially amenable to scale-up.

SUMMARY

Provided herein are methods of fabricating nano- and micro-structures, without requiring the cumbersome step of ex situ assembly. Also provided are nanostructures that are selectively created from a template base which is coated with a thin film of carbon or any other suitable material or combination thereof. Complex configurations and integrated structures can be produced by the selective removal of all, part, or none of the template base and deposited film. The fabrication method is amenable to mass, parallel production.

Also provided are integrated devices comprised of a template base that has a thin film residing parallel to its surface. The integrated devices are formed by heating a thin film forming fluid proximate to the surface of the template base in order to give rise to a thin film material. A portion of the template base adjacent to the thin film material is then removed to give rise to the thin film residing parallel to the surface of the template base.

Methods of fabricating a device comprising a thin film are also provided. These methods include the steps of: flowing a thin film forming fluid adjacent to a surface of a template base; contacting the thin film forming fluid in a region proximate to the surface of the template base to give rise to a thin film surmounting the surface of said template base; and selectively removing at least a portion of said template base that surmounts the thin film to expose the thin film.

Methods of transporting a fluid using an integrated capillary device are also provided. These methods comprise the steps of: providing an integrated capillary device and exerting the fluid through a lumen contiguous to the of the template base capillary and the thin film capillary. The integrated capillary device includes a template base capillary comprising a surface and a thin film capillary extending parallel from the surface of the template base capillary.

There are also provided methods of making electrical or ionic contact with an electron-conductive or ion-conductive medium. These methods comprise the steps of providing an electrode comprising a template base comprising a surface and an electrically conductive or ionically conductive thin film, said thin film extending parallel from the surface of the template base, at least a portion of the thin film surmounting the surface of the template base, and at least a portion of the thin film being exposed exterior to the template base; and contacting the portion of the exposed thin film with the electron-conductive or ion-conductive medium to effectuate electrical or ionic contact.

Further, there are provided methods of making photonic devices having a photon-conductive medium. These methods comprise the steps of providing a waveguide comprising a template base comprising a surface and a photonically-conductive thin film extending parallel from the surface of the template base and contacting a portion of the exposed thin film with the photon-conductive medium.

The summary and the following detailed description are exemplary and explanatory only and are not restrictive of the invention, as defined in the appended claims. Other embodiments will be apparent to those skilled in the art in view of the detailed description of the illustrative embodiments, examples, and additional illustrative embodiments as provided herein.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings:

FIG. 4 details the basic steps of producing a carbon-pipette electrode according to one embodiment.

FIG. 8a is schematic diagram of the current-voltage measurement apparatus used to characterize the transport of ions in solution through a sample fabricated nanopipette.

FIGS. 8b and 8c relate the I-V curves of electrolyte solution confined in carbon pipettes and in glass pipettes.

DETAILED DESCRIPTION OF ILLUSTRATIVE EMBODIMENTS

Figure 1:
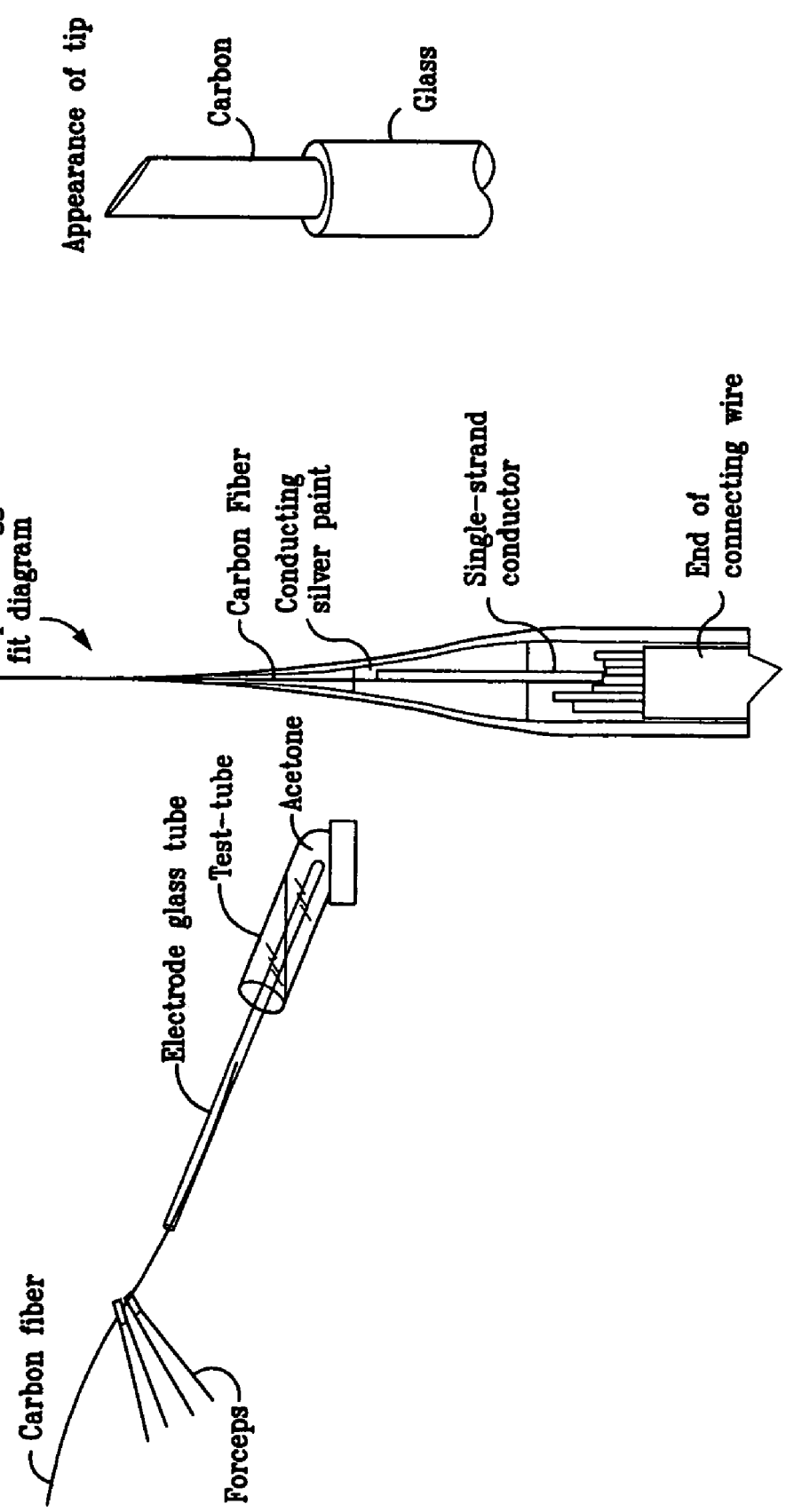
FIG. 1 presents a conventional prior art method of producing a carbon fiber electrode.
Figure 2:
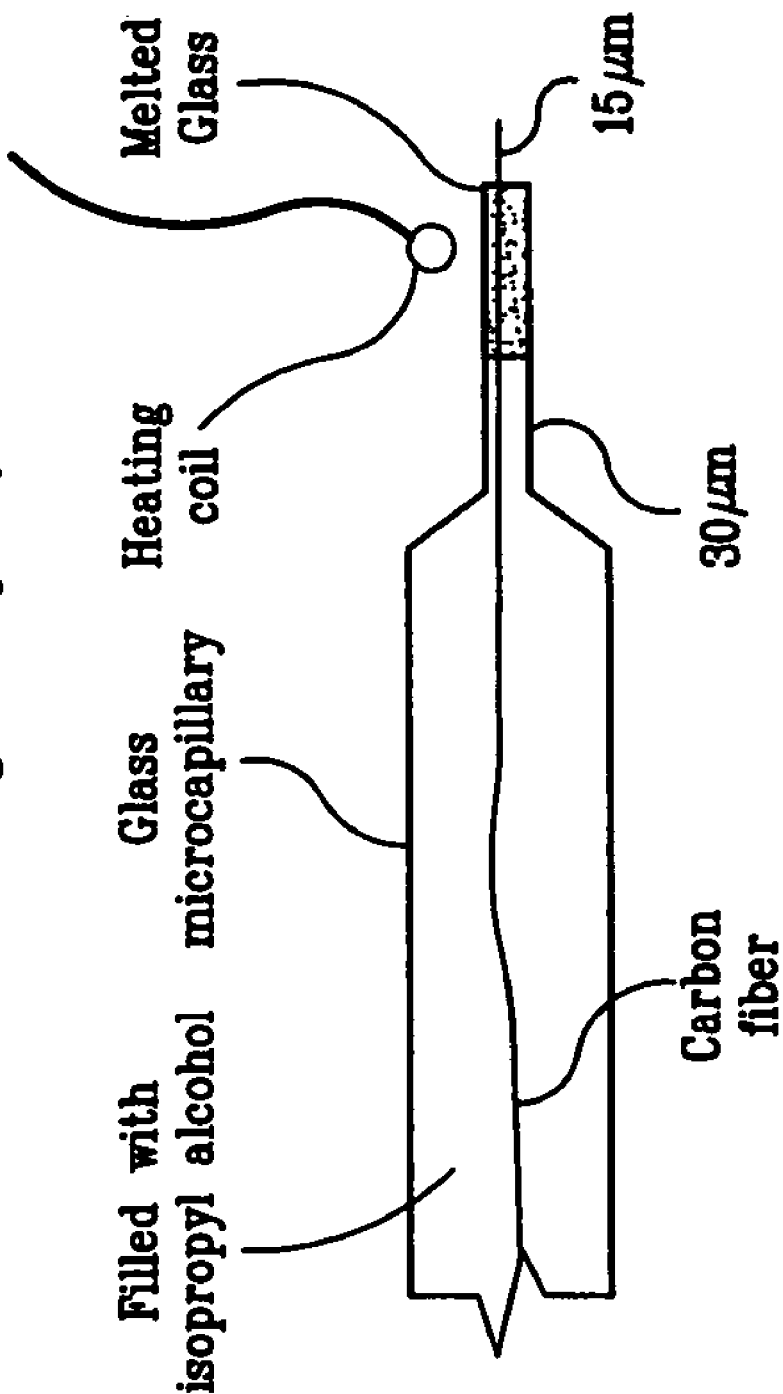
FIG. 2 presents a prior art method of affixing a carbon fiber to a glass capillary.

The present invention may be understood more readily by reference to the following detailed description taken in connection with the accompanying figures and examples, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

The integrated fabrication of structures in the nano- and micro-scale are provided throughout this detailed description. The nano- and micro-sized structures can be used in applications requiring smaller devices, such as, probing biological cells with minimal intrusion and transferring fluids or macromolecules on a nano-scale, a micro-scale, or both. As used herein, the term "nano-scale" typically means appertaining to a length scale having a characteristic dimension in the range of from about 0.1 nanometer ("nm") up to about 100 nm. As used herein, the term "micro-scale" typically means appertaining to a length scale having a characteristic dimension in the range of from about 0.1 micron ("µm") up to about 1000 µm.

The present invention allows for the fabrication of micro- and nano-structures made of carbon or other suitable materials, or combinations thereof, which are fabricated in situ. As one example, a single carbon pipette has been integrated with a glass capillary using the disclosed method. The methods disclosed herein are directly applicable to parallel production of nanostructure devices in mass.

Various embodiments of the present invention provide methods of fabricating integrated nanostructure devices comprising a thin film. These methods include flowing a thin film forming fluid adjacent to a surface of a template base; contacting the thin film forming fluid in a region proximate to the surface of the template base to give rise to a thin film surmounting the surface of said template base; and selectively removing at least a portion of said template base that surmounts the thin film to expose the thin film.

In certain embodiments of the present invention, the fabrication process starts with a template base that is made out of any material that can be shaped, formed, microfabricated, electrochemically etched, ion beam drilled, molded, cast, pulled, or any combination thereof Suitable template bases that can be used in the present invention include any material structure that is capable of being surmounted by a thin film. Suitable template base structures include a substrate, a film, a tube, a capillary, a channel, a rod, a cylinder, and the like. Suitable template base materials include glass, quartz, silicon, alumina, tungsten, titanium, ceramic, polymers, alloys, metals, or any combination thereof. In preferred embodiments, the template base is composed of a glass capillary or a quartz capillary. In certain embodiments, capillaries made of glass are heated, drawn, and separated to provide narrower capillary tubes having micro-scale tip openings. Suitable glasses include aluminosilicate glasses and borosilicate glasses. All types of glass can be used as a template material. Borosilicate glasses soften at lower temperatures compared to aluminosilicate glasses. Accordingly, thin films formed on borosilicate glasses can be formed at lower temperatures compared to using aluminosilicate glasses, for example, by using plasma-assisted CVD process. Carbon-based thin films can also form at room temperature by means of electrochemistry activated by sonication. Further details about template-based techniques for the fabrication of structures from carbon with sub-micron diameters can be found in Parthasarathy et al, 1995 *Adv. Mater.* 7 896; in Che et al, 1998 *Chem. Mater.* 10

260; and in Bradley et al, 2003 Chemistry Preprint Server, Misc. 1-6, CPS: *chemistry*/0303002 http://preprint.chemweb.com/chemistry/0303002.

In one embodiment, the thin films are used to form one or more integrated nano scale or micro-scale structures that are composed of the thin film material. These nano-scale or micro-scale structures can be suitably formed from any material that can be coated on the template base by means of vapor phase deposition, electroplating, electrochemistry, sonication, or any combination thereof. Suitable materials can be electrically conducting, semiconducting, insulating, or any combination thereof. For example, the nano- or micro-scale structures can be made of a conducting material, such as a metal, an electrically conducting polymer, carbon, or any combination thereof.

Suitable thin film forming fluids include conducting thin film precursor fluids, semiconducting thin film precursor fluids, superconducting thin film precursor fluids, insulating thin film precursor fluids, magnetic thin film precursor fluids, or any combination thereof. Suitable conducting thin film precursor fluids include any metal that can be applied as a thin film in various embodiments. Particular metals include gold, silver, platinum, aluminum, copper, nickel, chromium and any combination thereof. Suitable methods for depositing certain metals, such as nickel and chromium, include electroless electroplating.

Suitable forms of carbon thin films include amorphous, polycrystalline, crystalline, or any combination thereof. The various forms of carbon can be controlled by varying the process temperatures used. For example, at 670° C., a carbon thin film is largely amorphous. Polycrystalline carbon can be formed at about 900° C. Heating a carbon thin film (e.g., annealing) to about 1500° C. forms largely a crystalline carbon (i.e., graphite). The heating is preferably done in vacuum, in an inert gas environment (such as in argon), or both. The extent of the crystallinity of carbon thin films typically increases with the annealing temperature in the range of from about 600° C. to about 1500° C. Other suitable heating ranges include from about 700° C. to about 1300° C., and from about 800° C. to 1100° C. Optionally, catalysts can be provided on the surface of the template base to promote the formation of particular crystalline structures. The CVD process does not require any precoating to form a carbon film on a glass. The carbon synthesis is controlled largely through the growth temperature, the gas flow rate, and the type of precursor gas used. A catalyst can be used for forming a stand alone single or multi-wall carbon nanotube on a glass substrate. Suitable catalysts include iron, aluminum, molybdenum, nickel or any combination thereof. When using quartz as the template material, for example, a quartz capillary tube, iron oxide is a suitable catalyst. For example, iron oxide can be coated as a catalyst in the interior surface of a quartz tube to promote the growth of a crystalline carbon thin film. Typically, the shape of the thin film nano-scale or micro-scale structure is dictated by the shape of the template base upon which the thin film surmounts.

Any semiconducting material that can be coated on the template base can be suitably used for preparing the thin film. Any semiconductor thin film forming fluid composition that can be deposited, preferably using chemical vapor deposition, can be used as a thin film material. Suitable semiconducting compositions can be selected from Groups III, IV, V, and any combination thereof, from the Periodic Table. Suitable examples include Si, GaAs, SiGe, GaN, InAs, BN, and any combination thereof. In one embodiment of the devices of the present invention, for example, the template base can comprise surmounted thin films that provide nano- or micro-scale structures that are made of cadmium selenide ("CdS") and germanium ("Ge").

In some embodiments, the template base may also be surmounted by one or more thin films that give rise to one or more nano- or micro-scale structures that are composed of an insulating material. Suitable insulating materials include polymers, a nitride, such as silicon nitride, or silicon oxynitride.

In some embodiments the thin films have thicknesses in the range of from about 1 nm to about 1000 nm. The thin film thicknesses can also be in the range of from about 2 nm to about 500 nm, from about 5 nm to about 250 nm, from about 10 nm to about 100 nm, from about 20 nm to about 50 nm, or any combination thereof. In embodiments wherein the template base is a capillary tube, a thin film tube surmounting the interior surface of the capillary can be formed to provide an integrated nano-scale or micro-scale structure. In these embodiments, a capillary composed of the thin film is formed that has an outer dimension that is about the same as the inner dimension of the template base capillary. The inner dimension of the thin film capillary can be substantially smaller than the inner dimension of the template base capillary. For example, as more thin film forming fluid is deposited on the interior surface of the capillary, the thicker the thin film and the narrower the resulting opening in the thin film capillary. Accordingly, template base capillaries can have inner diameters of as small as about 5 microns, 2 microns, 1 micron (1000 nm), 500 nm, 300 nm and even as small as 100 nm using conventional capillary forming techniques known in the art. Additional details for the formation of micro-scale and nano-scale glass capillaries can be found in U.S. Pat. No. 5,788,166 to Valaskovic, et al., the portion of which pertaining to the formation of micro-scale and nano-scale glass capillaries for use in electrospray ionization ("ESI") is incorporated by reference herein. Subsequently, the outer template base capillary material can be removed using a suitable technique (e.g., etching glass materials using hydrofluoric acid) to give rise to an exposed thin film capillary. The length of the exposed thin film capillary can vary widely. In certain embodiments, the thin film capillary length can be anywhere in the range of from about 1 micron to about 200 microns, or in the range of from about 2 microns to about 100 microns, or from about 4 microns to about 80 microns, or from about 8 microns to about 70 microns, or from about 15 microns to about 60 microns, or from about 20 microns to about 50 microns. The resulting exposed thin film capillaries can have outer diameters of as small as about 5 microns, about 2 microns, about 1 micron (1000 nm), about 500 nm, about 300 nm and even as small as about 100 nm. The exposed thin film capillaries having even smaller outer diameters can be provided by removing a portion of the outer surface material of the exposed thin film capillary. Suitable methods of removing a portion of the outer surface material of the exposed portion of thin film capillaries include using a suitable chemical or plasma etch. Accordingly, thin film capillaries are readily formed having exposed outer diameters of as small as about 500 nm, and even as small as about 400 nm, about 300 nm, about 200 nm, about 100 nm, about 80 nm, about 60 nm, about 50 nm, about 40 nm, about 30 nm, about 20 nm, or even as small about 10 nm. Accordingly, the inner diameters of the thin film capillaries can be as small as about 500 nm, and even as small as about 400 nm, about 300 nm, about 200 nm, about 100 nm, about 80 nm, about 60 nm, about 50 nm, about 40 nm, about 30 nm, about 20 nm, about 10 nm, about 5 nm, about 2 m, or even as small about 1 nm. It is also envisioned that the inner diameter of a thin film capillary could be increased using a suitable etching methodology. For example, an etching compound can be contacted to the interior portion of the thin film capillary to remove material from inside the capillary. It is also envisioned in additional embodiments that a capillary template base will be completely filled with a suitable thin film forming material (i.e., no inner diameter, or the inner diameter is zero nm). Accordingly, a solid nano-scale or micro-scale probe or fiber can be formed having no lumen passing therethrough.

In certain embodiments in which the integrated structures include capillary template bases and thin film capillaries for use in probing (i.e., a nanoprobe or microprobe), manipulating (i.e., a nanomanipulator or micromanipulator), or transferring material (i.e., a nanopipe or micropipe) with biological cells, it is desirable that the dimensions of the thin film capillary portion are small enough to probe, manipulate, or both, one or more biological cells. As many biological cells are between about 1 micron and about 10 microns in size, it is desirable that suitable thin film capillaries have at least one dimension (i.e outer diameter, inner diameter, or length) that is about 10 microns or smaller. For example, a nanoprobe for assay the contents of a cell will have suitable outer diameter smaller than the cell in order to pierce the cell wall and contact the interior of the cell. In other embodiments the inner diameter of the thin film capillary nanoprobe will be large enough to transfer matter (e.g., electrolytes, nucleic acids, proteins, carbohydrates, or other small molecules such as a therapeutic agent) between the interior of the cell and the integrated device. Also, nanoprobes for measuring electric or ionic currents inside or on a cell suitably have outer diameters small enough to pierce or contact the cell wall.

In some embodiments, there are provided devices that include multi-probes that are arrayed or patterned in a controlled manner. As used herein, "arrayed or patterned in a controlled manner" refers to the ability to control the location of the thin film structures. For example, multiple thin film structures can be formed on the template base to form, for example a plurality of parallel probes. The plurality of parallel probes in the array may be functionalized in the same way or in different ways. The probes may be connected to a single reservoir or multiple reservoirs. Further details on preparing a plurality of parallel probes in this fashion is found in U.S. patent application Ser. No. 11/177,111, "Nanotube-Based Sensors And Probes", filed Jul. 8, 2005 by Bau et al., the portion of which pertaining to the preparation of sensors and probes is incorporated by reference herein.

On the surface of the template base, a thin film, or series of multiple films, is formed using any one of a variety of suitable film-forming methods. Suitable thin films can be provided by suitably applying a thin film forming fluid and then causing the fluid to form a solid-like thin film. Suitable thin film forming fluids include any of a variety of compounds that are known to provide thin film materials, examples of which include compositions of liquids, gases, or super-critical fluids that are capable of hardening upon forming covalent, ionic, or dispersive bonds upon heating, cooling, or any combination thereof. Examples of thin film forming fluids include a polymerizable organic species, such as ethylene, propylene, or styrene, inorganic compounds, such as a compound formed from any one of Groups II-IV, II-V, III-IV, or III-V in the Periodic Table, or any combination thereof. Suitable thin film forming fluids can be in the form of a liquid, a gas, or a super critical fluid. Suitable film-forming methods include flowing a suitable thin film forming fluid in a region proximate to the surface of a suitable template base. Suitable processes for flowing the fluids include vapor phase deposition, liquid phase deposition, electroplating, electrolysis or any combination thereof. In these processes, the fluids are suitably transported to a region proximate to a surface of a template base, which upon suitable conditions of heat, pressure, temperature and surface chemistry gives rise to the formation of a thin film surmounting the surface of the template base. In one embodiment, the thin film surmounting the template base typically includes covering at least a portion of the template base by the thin film. At least one thin film typically directly contacts the template base. In one embodiment, at least a portion of the thin film or films are then selectively removed by a method such as, oxidation in the presence of a plasma to expose at least a portion of the thin film. The template can then be selectively removed by a process such as, etching by acid, to expose the thin film. Selective removal can be carried out by applying a suitable etchant to a portion of the template base, for example, by dipping the template base in a suitable etching solution, by applying the etchant to only a portion of the template base, such as by selective coating or by use of a lithographic step, or any combination thereof. Etchants can be suitably removed from the template base using one or more washing steps.

In certain embodiments, the fabrication process starts with a template base in the form of a rod, cylinder or a capillary for producing a nanoprobe suitable for manipulating a nano-scale or micro-scale object. The resulting nanoprobes can be used for positioning a suitable material or biological matter. A wide variety of nano-scale and micro-scale objects can be manipulated using nanoprobes composed of a capillary template base and a thin film tube extending parallel from the capillary template base. For example, carbon nanotubes, semiconductor nanocrystals, titanium dioxide nanoparticles, polymer spheres, biological cells, unicellular organisms, biological cell components such as organelles (e.g., a cell nucleus, vacuole, membrane, mitochondria, endoplasmic reticulum, or portion thereof) can be positioned using the capillary nanoprobe tip.

Methods for fabricating devices that include a thin film are also provided. Several embodiments include the steps of flowing a thin film forming fluid adjacent to a surface of a template base and contacting the thin film forming fluid in a region proximate to the surface of the template base. Under thin film forming conditions of temperature, pressure and chemical reactivity, the proximity of the thin film forming fluid with the surface of the template base gives rise to a thin film surmounting the surface of the template base. Typically, the thin film remains contiguous with the surface of the template base material. Accordingly, these methods are typically followed by one or more steps of selectively removing at least a portion of said template base that surmounts the thin film to expose the thin film. In one embodiment, only a portion of the template base is removed from the thin film to give rise to an integrated nano-scale or micro-scale structure. The integrated structures can be a tube, sheet, shovel, fiber, or any combination thereof.

In certain embodiments, the thin film portion of the integrated structure forms a nano-scale or micro-scale tip. The tip can be in the form of a tube for transporting matter therethrough, or the tip can be a solid mass for contacting matter at the nano-scale or micro-scale. The tip is suitably composed of an inner thin film formed on the interior surface of a suitable template base, such as a capillary. Integrated structures that include a tip typically have the template base dimensions gradually change from a larger dimension in the capillary to the smallest dimension sat the tip of the thin film. Integrated structures are suitably used for dispensing and manipulating nano-scale particulate matter as well as atoms and molecules. Integrated structures can be used as probes in scanning probe microscopy applications, electrospray ionization ("ESI") sources, or as a probe that can penetrate cell membranes.

In one embodiment, all of the template base can be removed to give rise to a nano-scale or micro-scale stand alone structure comprising the thin film. Suitable stand alone structures include a tube, sheet, shovel, fiber, or any combination thereof. Stand alone structures can be formed from integrated structures by removing the template base.

In another embodiment, the template base (e.g., such as a capillary) further includes an interior surface and an exterior surface, wherein the thin film surmounts the exterior surface. In this embodiment, the method further includes the steps of selectively removing a portion of the thin film surmounting the exterior surface, and selectively removing a portion of the template base adjacent to the exterior surface. This embodiment is particularly useful where the template base is a capillary and a thin film is provided on the exterior and the interior of a capillary end. Removal of a portion of the thin film surmounting the exterior surface and the glass tip can give rise to a micro-scale or a nano-scale capillary tube thin film.

The methods provided herein may also be adapted to give rise to two or more thin films. For example, there is provided an embodiment of the method wherein the template base comprises an interior surface and an exterior surface, and the method further includes the steps of flowing a first thin film forming fluid adjacent to the interior surface of the template base and flowing a second thin film forming fluid adjacent to the exterior surface of the template base. This embodiment further includes the step of contacting the first and second thin film forming fluids in a region proximate to the interior and exterior surfaces of the template base, respectively, to give rise to first and second thin films surmounting the interior and exterior surfaces of the template base, respectively. Afterwards, the process includes the step of selectively removing a portion of said template base to expose said first and second thin films.

In embodiments wherein only a portion of the template base is removed, the resulting nano-scale or micro-scale integrated structures can be used for a variety of purposes. For example, carbon coated (both inside and outside) glass capillary integrated nano-scale and micro-scale structures can be used as nanoelectrodes to probe electrical properties of nanostructures. Carbon coated glass capillaries can also be used as a scanning tunneling microscope ("STM") tip, for example, to map out the charge density of states of a conducting material. One can also use the carbon coated glass capillary integrated structures of the present invention to measure electrical and/or electrochemical activities inside of a cell while exchanging fluids through it. The integrated nanoscale and micro-scale structures of the present invention can also be used to dispense minute droplets of fluids for surface patterning and for the deposition of nanodrops laden with macromolecules. The droplets can also be laden with proteins, oligonucleotides, functionalized nanoparticles, or any combination thereof, to form arrays that are used in biodetection methodologies.

Variations of these methods are also provided. For example, one embodiment provides a method wherein a plurality of thin film forming fluids are heated to provide a plurality of thin films surmounting the surface of said template base to give rise to a multilayer structure that is integral to said template base. In yet another embodiment, a portion of said template base is removed to expose said multilayer structure. This method may further include the step of selectively removing a portion of a thin film or of the multilayer structure. A suitable step of removing a portion of the thin film can include an oxidative process. Suitable oxidative processes include exposing the thin film to an oxygen plasma, a heated oxygen gas, an electrochemical redox process, or any combination thereof. Exposure of thin films to an oxidizing process typically gives rise to oxidation products that otherwise could be a source of contamination. Accordingly, certain embodiments of the methods of the present invention further include the step of removing oxidation products.

In various embodiments, the template base may be composed of a metal, glass, plastic, ceramic, semiconductor, such as silicon, or any combination thereof. Suitable template base materials may be composed of quartz, silicon, alumina, tungsten, titanium, or any combination thereof. In a one embodiment, the template base is a capillary. Suitable thin films are capable of being formed using vapor phase deposition, liquid phase deposition, electroplating, electrolysis or any combination thereof. Typically the methods further include the step of heating the thin film forming fluid to give rise to the thin film. Suitable thin film forming fluids can be a liquid, gas, supercritical fluid, or any combination thereof. Suitable thin films can be electrically conducting, superconducting, semiconducting, insulating, or any combination thereof. Suitable conducting materials include gold, silver, platinum, aluminum, copper, indium, tin, an electrically conductive polymer, nickel, chromium, and any combination thereof. Suitable materials can be nonmagnetic, ferromagnetic, paramagnetic, or any combination thereof. Any conducting material that can be formed by chemical vapor deposition or electroplating, or any combination thereof, can be suitably used.

Certain embodiments include devices in various forms, including, an annulus of deposited films, a tube, a pipette, a shovel, a scalpel, or a sheet. Certain embodiments of devices can be used as an electron beam source, scriber, spring, scalpel, or syringe. Other embodiments can be used as electronic, optoelectronic, or electromechanical devices. In certain embodiments, various suitable molecules, such as macromolecules, oligonucleotides, proteins, antibodies, and the like, as well as any combination thereof, can be attached as ligands to provide functionalized devices. These functionalized devices may suitably be used in biosensors or to extract or introduce material from a biological cell. Established chemistries known to those skilled in the art, for example, attaching biotin or avidin to carbon, can be readily adapted to attach ligands to the thin films as provided herein. For example, when a thin film tip is coated with gold, there are well established linking chemistries, for example, those involving sulfur, for attaching macromolecules such as proteins, oligonucleotides, antibodies, or any combination thereof to the gold tip. A variety of different types of measurements can be made using the biosensors. For example, there is a great interest in nano-electrodes for measuring the I-V characteristics of electrolytes. The devices can also be used as proximity scanning probes based on electrochemical principles. The devices can also be used as a fabrication tool.

Various electronic devices, optoelectronic devices, electromechanical devices, or any combination thereof can also be prepared according to the methods provided herein. For example, in monitoring an electrical response, one can measure the change in a functionalized carbon thin film tube's resistance as the functionalized tube's surface interacts with biomolecules of interest. Measurement of charge transfer during the biomolecular binding process gives rise to the biosensing functionality. In monitoring a mechanical response, one can measure the mass change of the tube by measuring the extent of the bending that the biomolecules exert on the functionalized tip. In monitoring an optical response, one can sense the presence of biomolecules by detecting fluorescence signals using the functionalized carbon tip of a nano-scale or micro-scale integrated structure.

In certain embodiments where portions of the thin film or template, or combinations thereof, are selectively removed, devices exhibiting pores, slits, perforations, or combinations thereof, may be produced. In other embodiments, patterned portions of the thin films or templates can be selectively removed to form a filigree structure.

In another embodiment, one or more of a variety of macromolecules, for example, oligonucleotides and proteins, can be attached to the nanoprobes for use in chemical sensors, biosensors, or both. Nanoprobes having one or more of a variety of macromolecules, for example, oligonucleotides and proteins, can be attached to the nanoprobes for transporting material into or out of a cell. Suitable nanoprobes for transporting materials to and from cells may, or may not, include a hollow tube-like lumen for liquid dispensing uses.

In another embodiment, well-controlled arrays of nanopipettes are provided. In these embodiments the nanopipettes arrays comprise a plurality of nanopipettes, each of the nanopipettes comprising a thin film nano-scale or micro-scale tube, wherein each of the nanopipettes are positioned at a predetermined location in an array. The nanopipette arrays can be fabricated by providing an array of capillary tubes and contacting each of the capillary tubes to a thin film forming fluid under conditions that gives rise to the formation of a thin film surmounting each of the capillary tube ends, and removing at least a portion of each of the capillary tube ends to give rise to a plurality of nanopipettes. The nanopipettes arrays can be used, for example, in biosensing, in dispensing of minute drops for surface patterning, and surface scribing.

Also provided are methods for transporting a fluid in an integrated capillary device. Certain embodiments of these methods include the steps of exerting a fluid through the lumens of the template base capillary and the thin film capillary of a provided integrated capillary device that includes a template base capillary and a thin film capillary extending parallel from the surface of the template base capillary. In some embodiments of the invention, the thin film capillary is in fluid communication with a biological cell and the method includes exerting a fluid between the thin film capillary and the biological cell. Related methods include the steps of providing an integrated capillary device, comprising: a template base capillary comprising a surface; and a thin film capillary extending parallel from the surface of the template base capillary, at least a portion of the thin film capillary surmounting the surface of the template base capillary, and at least a portion of the thin film capillary exposed exterior to the template base capillary; and exerting the fluid through a lumens of the template base capillary and the thin film capillary. In some embodiments of these methods, the thin film capillary is in fluid communication with a biological cell and fluid is exerted between the thin film capillary and the biological cell. Accordingly, methods of depositing nanodrops on surfaces for surface patterning are also provided by the present invention. In certain embodiments, the disclosed methods includes dispensing nanodrops laden with suitable materials such as macromolecules, oligonucleotides, and nanoparticles. These materials can be functionalized or unfunctionalized particles.

Also provided are methods of making electrical or ionic contact with an electron-conductive or ion-conductive medium. These methods include the steps of: providing an electrode, comprising: a template base comprising a surface; and an electrically conductive or ionically conductive thin film. In these methods, the thin film extends parallel from the surface of the template base, wherein at least a portion of the thin film surmounts the surface of the template base, and at least a portion of the thin film is exposed exterior to the template base. Electrical or ionic contact is then effectuated by contacting the portion of the exposed thin film with the electron-conductive or ion-conductive medium. These methods may further include the step of transporting electrons, ions, or both between said exposed thin film and said electron-conductive or ion-conductive medium. In these methods, the electron-conductive medium may also comprise a metal or a semiconductor. In other embodiments, the ion-conductive medium may comprise an aqueous medium. Suitable aqueous media comprises water, extracellular fluid, intracellular fluid, or any combination thereof. Alternate embodiments may include a metal or semiconductor residing on an electronic component.

There are also provided methods of making photonic contact with a photon-conductive medium. These methods comprise the steps of providing an waveguide, comprising: a template base comprising a surface; and a photonically conductive thin film, said thin film extending parallel from the surface of the template base. In these methods at least a portion of the thin film surmounting the surface of the template base, and at least a portion of the thin film exposed exterior to the template base. Finally, the portion of the exposed thin film is contacted with the photon-conductive medium to effectuate photonic contact.

The devices disclosed herein have myriad uses, including nanoelectrodes, functionalized probes, biosensors, and nanopipettes for fluid and macromolecule transfer, in particular, for application to biological cells. In one embodiment, proteins, antibodies, oligonucleotides, or any combination thereof, can be attached to the nanopipette for use as a biosensor, a means to probe a biological cell's interior, to introduce or pull out ions or molecules, or any combination thereof. In certain embodiments, an integrated structure fabricated by a method of this invention can be used as a conductive electrode. In other embodiments, there is provided a method for making photonic or electrical contact with a medium. In certain embodiments, fluidic devices produced by the disclosed methods may be used to sense and exchange material within the interior of biological organisms, on a cellular and cell nucleus level, with minimal intrusion and a high precision of placement. In certain embodiments, functionalized probes produced according to the methods disclosed herein can be used for inserting proteins or enzymes into a biological cell or for chemical sensing in the cell or cell organelle. Other embodiments of nanostructures formed by the disclosed methods may also be suitably used as tips for atomic force microscopes.

In certain embodiments, the nanopipettes and other devices fabricated with the disclosed methods may be readily filled with particle suspensions, liquid emulsions, liquids, macromolecules, small molecules, analytes, or any combination thereof. A variety of devices made according to the various aspects of the present invention are characteristically transparent when filled with a fluorescent suspension.

EXAMPLES AND ADDITIONAL ILLUSTRATIVE EMBODIMENTS

Figure 3:
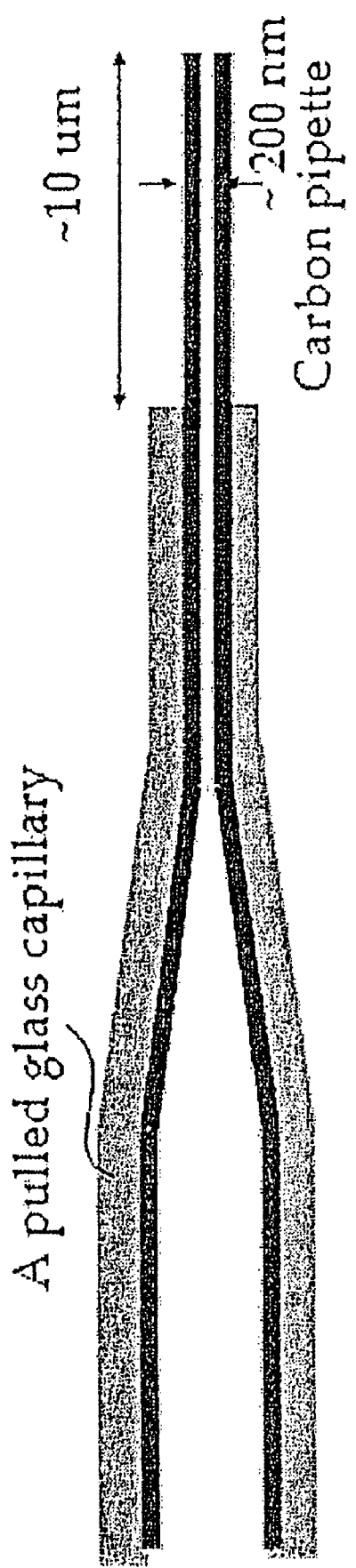
FIG. 3 illustrates an embodiment of the structure of a carbon pipette as formed by one of the disclosed methods.

The disclosed methods have been used to produce integrated nanostructure devices using ethylene as the thin film forming fluid to form a carbon thin film, and using pulled and formed glass capillaries as the template base. A fabrication process can use a commercially available capillary that is open at one or both ends. For example, a suitable capillary can be made of a standard material such as aluminosilicate glass and have an outer diameter of about 1 mm and an inner diameter of about 0.6 mm. To prepare the template base, a suitable capillary is typically reduced in size. A heat source can be used to heat a section of the glass capillary. In one embodiment, an electrical resistor was used to externally heat the glass section. Above the glass-softening point, the capillary can be pulled from both ends to reduce the inner and outer diameters to the desired size for the template. At the end of this process, the capillary is separated into two pieces with each pulled piece having one end shaped in the desired dimensions and form of a tip. This tip shape and dimension is determined by the pulling force and heating temperature used in the pulling process. A commercial micropipette puller as known in the art was used to reduce the diameter of the capillary and produce the tapered end with the desired dimensions and shape. Capillaries with tapered ends with inner diameters of hundreds of nanometers have been fabricated. An example of a pulled glass capillary as part of the final integrated nanostructure is shown in FIG. 3.

Once the capillary has been pulled to size, a material is deposited on the surface of the inner and outer diameters. This process can be accomplished using chemical vapor deposition or electroplating. FIG. 4 depicts the sequence of fabrication of an integrated carbon-pipette nanostructure. The capillary is placed in a oven heated to a prescribed temperature in an inert gas environment, for example Argon ("Ar"). In one embodiment, a carbon containing fluid is used as the deposited material, but other materials that can be chemically vapor deposited could be used to produce the film layers on the template. For certain embodiments, carbon to deposit on the capillary, the oven temperature is generally high enough to induce chemical vapor deposition but below the softening point of the template base material. For aluminosilicate glass the softening temperature is approximately 670° C.

At temperature, the gas flow is switched to a premixed carbon-rich feedstock. This feedstock gas can be any carbon rich gas such as ethylene, or ethylene mixed with an inert gas. The formation of the carbon film on the surface of the template is initiated by the introduction of this gas mixture. The outer diameter of the inner carbon layer is typically controlled by the inner diameter of the capillary template, and the thickness of the carbon film is controlled by the timed exposure of the surface in the heated feedstock gas environment. For optically transparent template base materials, the optical transparency of the glass capillary was observed to change from lucid through varying degrees of opacity as the carbon deposition time was increased. Carbon layers ranging from about 15 nm thick after about 6 hours, 30 minutes of deposition time to about 50 nm thick after about 16 hours of deposition time were achieved. Carbon film deposited on the surface of the capillary during this stage of the process is depicted in FIG. 4b.

Following the steps as shown in FIG. 4, the carbon coating can then be selectively removed by any of a variety of methods known in the art, such as the oxidation of carbon in the presence of an oxygen plasma. A commercial plasma etcher was used to provide a sufficiently directional plasma so that the carbon coating on the inner surface of the template at the tapered end was not affected by this removal step. A depiction of an embodiment where the carbon has been removed on the outer surface can be seen in FIG. 4c. The tip of the template itself can then be removed to expose the surface of the carbon tube formed on its inside. For example, a glass template was dissolved by controllably dipping the device end in hydrofluoric acid. The remaining structure for certain embodiments, a capillary with an integrated carbon pipette, is depicted in FIG. 4d.

Figure 5:
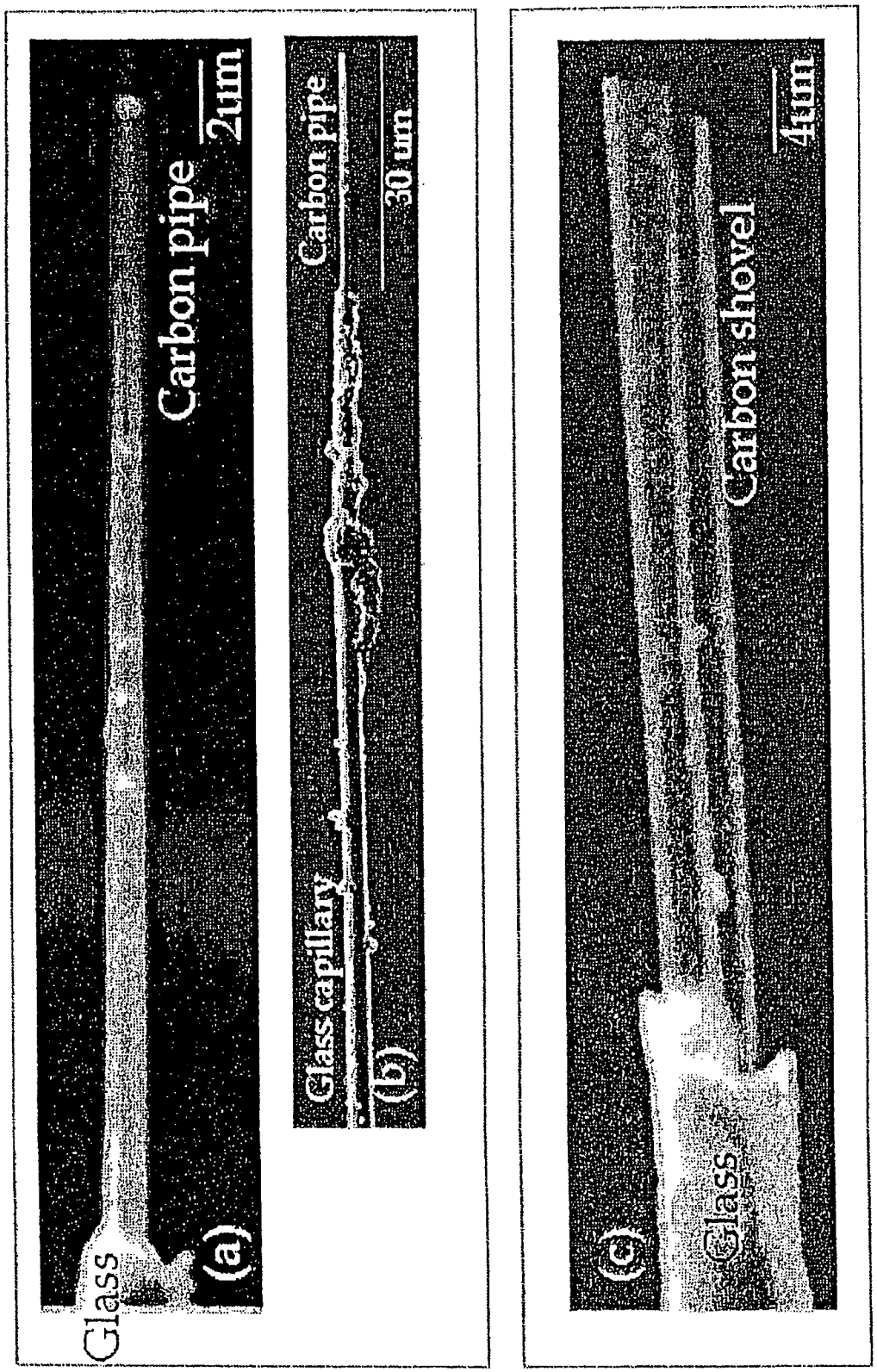
FIG. 5 presents SEM images of integrated carbon-pipette electrodes and a carbon shovel produced according to one embodiment.
Figure 6:
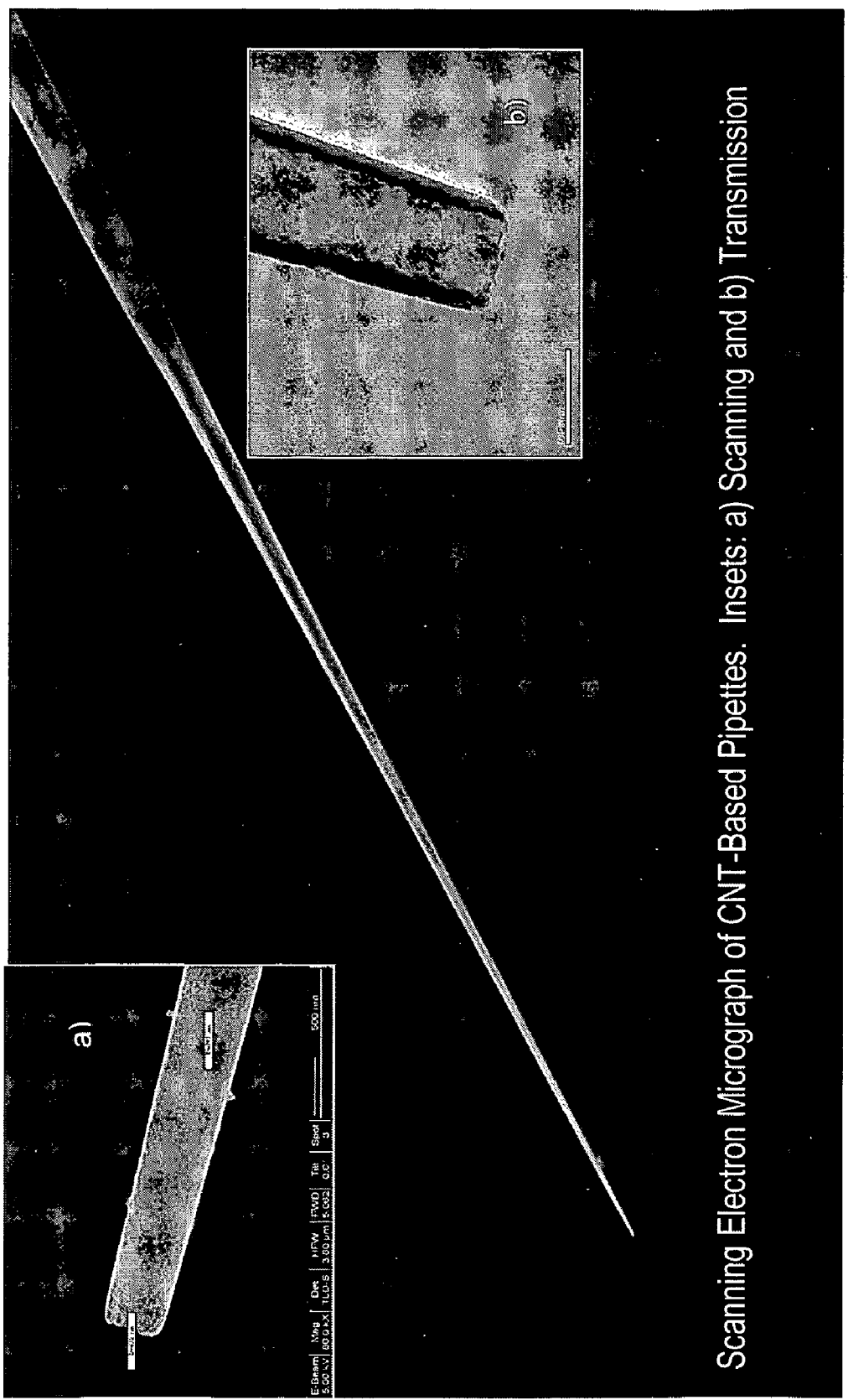
FIG. 6 shows a SEM image of a carbon-nanotube-based pipette with insets a) and b) detailing magnified pipette tips.
Figure 7:
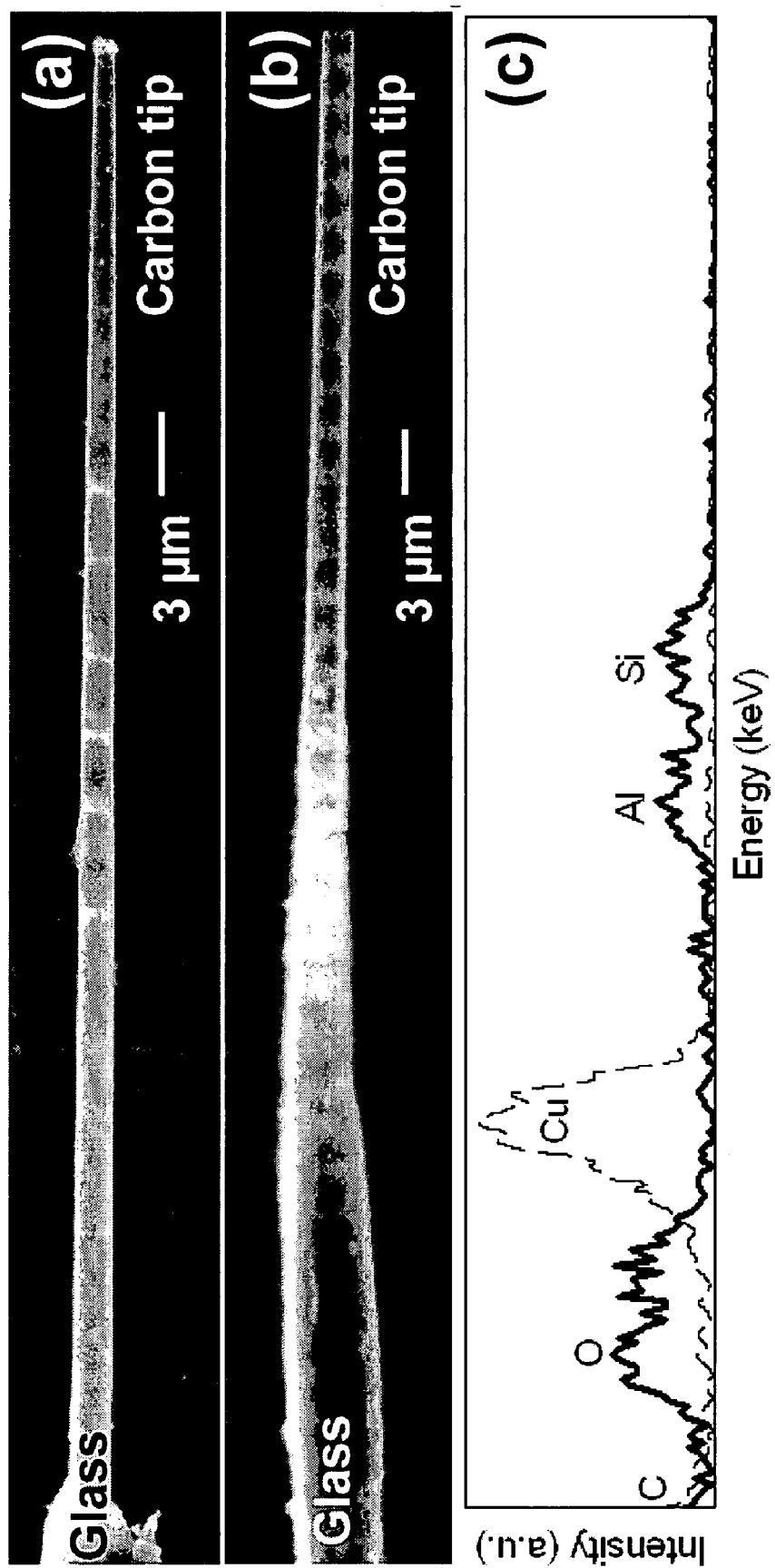
FIGS. 7a and 7b depict SEM images of devices fabricated according to one method.
FIG. 7c presents EDS spectra corresponding to the composition of the surface of the carbon tip and the glass portion of the capillary of a device fabricated according to one method.

FIG. 5a shows a scanning electron microscope (SEM) image of a representative integrated carbon pipette and glass capillary structure fabricated according to the above method. The carbon structures formed appear transparent in the SEM images, whereas the capillary glass appears white. The scanning electron beam passes through the thin, conducting carbon, but charges the insulating dielectric glass. The carbon pipette in FIG. 5b measures approximately 1 micrometer in diameter and 30 micrometers in length with a wall thickness about 100 nanometers. As noted above, the dimensions of the carbon structure can be controllable by adjusting parameters in the process. As shown in FIG. 5, the carbon structure of an example embodiment, which can protrude significantly from the template end, is an integral part of the template. Another SEM image of an example nanostructure produced by the disclosed methods appears in FIG. 6. As seen in the magnified insets a) and b), the tip of this example embodiment forms an open-ended carbon pipette. For the pipette tip shown in the upper inset of FIG. 6, the smallest diameter of the pipette was measured to be 632 nm. Other examples of SEM images of nanostructures produced by this fabrication method appear in FIG. 7. In FIG. 7a the apex of the carbon pipette has a diameter of about 700 nm, a wall thickness of about 50 nm, and a length of about 40 microns. A shorter carbon pipe of approximately 20 microns in length is shown in FIG. 7b. The diameter at the apex of the carbon pipe in this structure is approximately 1.5 microns and the wall thickness is about 50 nm. As shown in FIGS. 6 and 7, the glass portion of the structures are slightly tapered to meet the carbon tip. Variations in the dimensions of the carbon pipette can be controlled by adjusting process parameters such as the glass pulling force and resultant capillary diameter, the heating temperature and the glass etching time. Tube diameters as small as 100 nm can be produced by controlling these process parameters.

In other embodiments, the template base can be shaped in a variety of forms in addition to pipes. Varying the initial template can be used to produce integrated carbon structures in the shape of carbon shovels as shown in FIG. 5c, carbon sheets or scalpels. Shovels, sheets, and scalpels can be formed by depositing the carbon layer on a template in the corresponding shape or by opening a carbon pipette along its length after it is fabricated on a standard capillary. The disclosed fabrication method is easily adaptable to varied shapes and sizes of creative nanostructures. One example of a more complex structure is a pipe that consists of two walls of carbon separated by an annulus. This structure is formed by depositing a layer of carbon on the inside and outside wall of a capillary and then etching away the capillary material, leaving behind the carbon walls. In this and other embodiments, the fabrication method does not necessarily include the step that removes the thin film residing on the surface of the template base. In certain embodiments, only the template base material is removed. Even more complex shapes and patterned structures can be fabricated in other embodiments by selectively removing all, part, or none of the template base or thin film, or films. Other embodiments include removing material only at one end of the structure, while others remove material from both ends or from along a length of the integrated structure.

In addition to aluminosilicate as a template base material, another embodiment of the invention can use silicon as the template base material. Carbon-tube-based probes for use in atomic force microscopy can be fabricated from carbon films deposited on silicon templates that have then been etched to remove part of the silicon base. Other complex templates can be fabricated with silicon, which enables further embodiments of the invention resulting in the generation of diverse integrated nanostructures—structures with pores, slits, or intricately patterned carbon filigree. In addition to glass and silicon, another embodiment of the invention may use quartz as the template material. Yet another embodiment may use alumina as the material for the template. Further embodiments contemplate the use of titanium or tungsten as the template material. Generally, any material that can be shaped and formed may be used to fabricate the template. The template may also be precoated with material before the deposition step. In certain embodiments, the template may be coated with a catalyst.

In certain embodiments, removal of the template material, whether silicon, glass, or other suitable material, can be selectively controlled to produce patterned integrated nanostructures with varied configurations of template base material and thin film material along the length of the device.

In addition to the disclosed embodiment using carbon as the chemically deposited vapor, the method disclosed may be practiced with any material suitable for chemical vapor deposition. For carbon itself, the deposition step may be practiced at higher temperatures to achieve crystalline forms of carbon formed as walls. Graphite, for example, may be formed at these higher temperatures. Other embodiments of the invention may use a semiconductor such as CdS or Ge to form the film layer on the template. Further embodiments may deposit a layer of an insulator such as nitride on the template.

In other embodiments, the inventors also contemplate using electroplating, electrolysis, or any other known metal coating techniques in the art to produce the film layer on the template. Embodiments using electroplating may be produced with any material that is suitable for electroplating. Such embodiments may include the use of gold, silver, platinum, aluminum, or copper layers on the template. As shown, the fabrication method may be applied to prepare nanostructures of varying sizes and shapes, using a wide variety of materials as the template, and a range of materials as the film layers.

As shown, this fabrication method can produce varied shapes of integrated nanostructures based on the initial shape and dimension of the template that is used in the deposition step. The thin film typically replicates the shape of the chosen template. The process can readily be extended for use in mass, parallel fabrication of integrated nanostructures.

A device fabricated by the disclosed methods has been characterized by exposing the device to energy dispersive x-ray spectroscopy (EDS) to determine the composition of the device's surface. The solid line in FIG. 7c is a representative EDS spectrum of a section of the surface of the device that appears whitish in SEM imaging. As shown, the spectrum indicates that this surface is composed of Si, O, and Al, which is consistent with the aluminosilicate glass that was used as the template. The dotted line in FIG. 7c represents an EDS spectrum taken from the tip of the device. This spectrum is devoid of the peaks associated with the constituent elements of glass. Carbon and copper (Cu) peaks are shown. The Cu signal indicates that the walls of the tip are sufficiently thin and electrically conducting to appear translucent to the scanning electron beam because the Cu peak originates from a Cu strip positioned about 500 microns beneath the tip as part of the sample holder.

In one embodiment, using a carbon-containing thin film forming fluid to produce nanopipettes was found to give rise to significantly better electrical conductors than that of a glass capillary. The electrical resistance of the resulting carbon thin film was measured by direct contact to be approximately 5000 $\Omega$ cm$^{-1}$, compared to that of the glass capillary which has resistance of greater than $10^{12}$ $\Omega$ cm$^{-1}$. The thin film pipettes were found to be better electrical conductors than a 0.1 M KCl aqueous, electrolyte solution, which has an electrical resistance estimated around 26,000 $\Omega$ cm$^{-1}$.

To demonstrate that the carbon nanopipettes fabricated by the disclosed methods can be used to transport ions, the current-voltage (I-V) characteristics were measured by filling the pipettes with a 0.1 M KCl electrolyte solution. Measurements from glass capillaries without carbon deposition were used for comparison. FIG. 8a is a schematic of the I-V measurement apparatus used to characterize the transport of ions through the pipes. As shown, a nanopipette filled with 0.1 M KCl solution was partially submerged in a bath of the same electrolyte solution. One Pt electrode was submerged in the capillary electrolyte solution and another Pt electrode was placed in the bath. A linear voltage sweep at the rate of 5 mV s$^{-1}$ was applied by an HP 4145B parameter analyzer and the corresponding current was recorded. The I-V curves for three carbon and three glass pipes are depicted in FIGS. 8b and 8c, respectively. The tips of the pipes tested had diameters larger than, approximately equal to, and smaller than one micron, based on optical microscope measurements. The pipe diameters used were much larger than the thickness of the electric double layer. Reproducible I-V curves were achieved.

In contrast with the I-V curves of the glass pipes, the I-V data depicted for all three carbon pipes in FIG. 8b exhibited a noticeable change in the ionic conductivity around 0.3 V with a nearly linear increase in the current response when the potential difference between the two platinum electrodes was larger than 0.3 V. The I-V curves of the electrolytes in the glass pipes depicted in FIG. 8c exhibited Ohmic-like I-V dependencies over the entire voltage range used in the measurements. Without being bound to any theory of operation, the change of slope observed in FIG. 8b is a suspected result of a Faradaic reaction between the carbon wall and the solution. After a threshold potential has been reached, charge transfer occurred across the interface of the carbon surface and the solution as the carbon provided a parallel path to current flow. Without being bound to any theory of operation, nonlinear I-V curves apparently demonstrate that once a threshold potential has been exceeded, electric current can pass from the solution to a metal lining and back into solution, resulting in nonlinear I-V curves.

Figure 9:
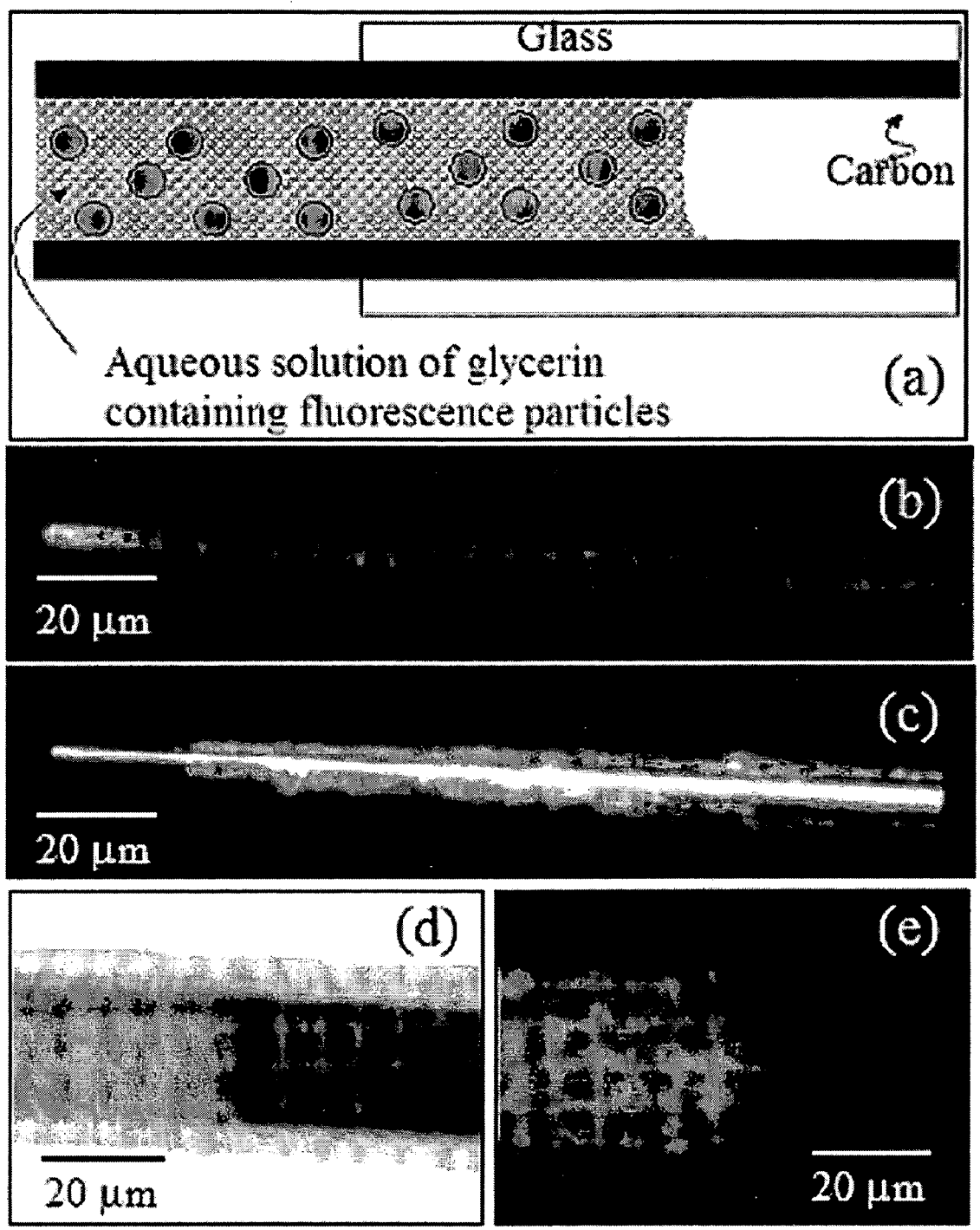
FIG. 9a shows a schematic diagram of a carbon pipette partially filled with a suspension of fluorescent particles.
FIGS. 9b and 9c present the corresponding optical and fluorescent images, respectively, of a partially filled pipette.
FIGS. 9d and 9e show the optical and fluorescent images, respectively, of an air-suspension interface inside a pipette.

Carbon nanopipettes fabricated by the disclosed methods also display transparency to optical and fluorescent light. The process of filling the nanopipettes with various liquids was observed through the carbon wall. FIG. 9 shows a tube that has been filled by capillary imbibition with a glycerin-water suspension of fluorescent particles of about 50 nm in diameter. The dye is incorporated in the polystyrene core with a fluorophore solution. FIG. 9a is a schematic diagram of the cross-section of a carbon nanopipette partially filled with this suspension of fluorescent particles. A fluorescent image of a portion of the pipette tip that is filled with the suspension can be seen in FIG. 9b, and FIG. 9c is a 400× optical image of the corresponding fluorescent image. The interface of the suspension with air inside the carbon pipette is shown in the optical image of FIG. 9d. A complementary fluorescent image of this interface is shown in FIG. 9e. The fluorescent signal is clearly visible through the pipette wall. As observed, the pipettes are also readily filled with the suspension without trapping air bubbles within the pipette. The ability to fill the tubes with particles allows for a means of synthesizing new materials and endowing the tubes with new properties.

What is claimed:
1. An integrated device, comprising:
a hollow, macroscopic handle comprising a first material, the handle tapering to a distal end, the handle having at a point along its length an exterior cross sectional dimension of from about 100 micrometers to about 5 mm, the distal end of the handle comprising an interior cross-sectional dimension in the range of between about 100 nm to about 10 micrometers, wherein the first material comprises glass, quartz, silicon, plastic, or any combination thereof;

a capillary probe or fiber probe of a second material, said capillary or fiber probe conforming to at least a portion of the inner surface of the hollow macroscopic handle at the distal end, and the second material comprising a carbonaceous material, a metal, a semiconductor, or any combination thereof.

2. The integrated device of claim 1, wherein the hollow, macroscopic handle comprises a material capable of being shaped into a tapered, hollow form.

3. The integrated device of claim 1, wherein the carbonaceous material comprises amorphous carbon, polycrystalline carbon, graphite, crystalline carbon, or any combination thereof.

4. The integrated device of claim 1, wherein the metal comprises gold, silver, platinum, aluminum, copper, chromium, nickel, or any combination thereof.

5. The integrated device of claim 1, wherein the semiconductor comprises an element selected from Group III, Group IV, Group V, or any combination thereof.

6. The integrated device of claim 1, wherein at least a portion of the second material is exposed exterior to the distal end of the hollow macroscopic handle.

7. The integrated device of claim 1, wherein the portion of the second material exposed exterior to the distal end of the hollow macroscopic handle comprises an exterior cross-sectional dimension in the range of from about 10 nm to about 100 microns.

8. The integrated device of claim 1, further comprising a connector placing the second material in electrical communication with the environment exterior to the integrated device.

9. The integrated device of claim 1, further comprising a source of fluid placing the distal end of the exposed portion of the second material in fluid communication with the interior of the hollow macroscopic handle.

10. The integrated device of claim 1, wherein the distal end of the handle comprises an interior cross-sectional dimension in the range of between about 200 nm to about 2 micrometers.

11. An integrated device, comprising:

a hollow, macroscopic handle comprising a first material, the handle tapering to a distal end, the handle having at a point along its length an exterior cross sectional dimension of from about 100 micrometers to about 5 mm, wherein the first material comprises glass, quartz, silicon, plastic, or any combination thereof, a capillary probe or fiber probe comprising a second material, the capillary or fiber probe conforming to at least a portion of the inner surface of the hollow macroscopic handle, at least a portion of the capillary probe or fiber probe being exposed beyond the distal end of the macroscopic handle, the exposed portion of the capillary probe or fiber probe having an exterior cross-sectional dimension in the range of from about 10 nm to about 10 microns, and the second material comprising a carbonaceous material, a metal, a semiconductor, or any combination thereof.

12. The integrated device of claim 11, wherein the hollow, macroscopic handle comprises a material capable of being shaped into a tapered, hollow form.

13. The integrated device of claim 11, wherein the carbonaceous material comprises amorphous carbon, polycrystalline carbon, crystalline carbon, or any combination thereof.

14. The integrated device of claim 11, wherein the metal comprises gold, silver, platinum, aluminum, copper, chromium, nickel, or any combination thereof.

15. The integrated device of claim 11, wherein the semiconductor comprises an element selected from Group III, Group IV, Group V, or any combination thereof.

16. The integrated device of claim 11, further comprising a connector placing the second material in electrical communication with the environment exterior to the integrated device.

17. The integrated device of claim 11, further comprising a source of fluid placing the distal end of the exposed portion of the second material in fluid communication with the interior of the hollow macroscopic handle.

* * * * *

UNITED STATES PATENT AND TRADEMARK OFFICE
CERTIFICATE OF CORRECTION

| | | |
|---|---|---|
| PATENT NO. | : 7,824,620 B2 | Page 1 of 1 |
| APPLICATION NO. | : 11/231425 | |
| DATED | : November 2, 2010 | |
| INVENTOR(S) | : Haim H. Bau et al. | |

It is certified that error appears in the above-identified patent and that said Letters Patent is hereby corrected as shown below:

In the Claims

<u>Column 17,</u>
Claim 7:
Line 33, delete "claim 1" and insert -- claim 6 --.

Signed and Sealed this
Twentieth Day of May, 2014

Michelle K. Lee
*Deputy Director of the United States Patent and Trademark Office*